(12) United States Patent
Schaewe et al.

(10) Patent No.: US 11,839,433 B2
(45) Date of Patent: Dec. 12, 2023

(54) SYSTEM FOR GUIDED PROCEDURES

(71) Applicant: Medtronic Navigation, Inc., Louisville, CO (US)

(72) Inventors: Timothy J. Schaewe, Nederland, CO (US); Yvan Paitel, Louisville, CO (US); Neil F. Straka, Boulder, CO (US); Bryan Wilson, Westminster, CO (US)

(73) Assignee: Medtronic Navigation, Inc., Louisville, CO (US)

(*) Notice: Subject to any disclaimer, the term of this patent is extended or adjusted under 35 U.S.C. 154(b) by 107 days.

(21) Appl. No.: 15/272,808

(22) Filed: Sep. 22, 2016

(65) Prior Publication Data

US 2018/0078316 A1 Mar. 22, 2018

(51) Int. Cl.
*A61B 34/20* (2016.01)
*A61B 34/10* (2016.01)
(Continued)

(52) U.S. Cl.
CPC ............ *A61B 34/20* (2016.02); *A61B 5/0035* (2013.01); *A61B 5/7435* (2013.01); *A61B 34/10* (2016.02);
(Continued)

(58) Field of Classification Search
CPC ... A61B 34/20; A61B 2090/365; A61B 1/043; A61B 5/0071; A61B 6/487; A61B 34/25; A61B 5/0035; A61B 90/36; A61B 5/7435; A61B 90/37; A61B 34/10; A61B 2090/3762; A61B 2576/026; A61B 2018/00446; A61B 2017/00203; A61B 2017/00199; A61B 2090/374; A61B 2505/05; A61B 5/7445; A61B 2034/2055; A61B 2034/2051; A61B 2090/368; A61B 2034/107; A61B 2560/0475; A61B 2034/2068; A61B 2090/367;
(Continued)

(56) References Cited

U.S. PATENT DOCUMENTS 4,395,731 A * 7/1983 Schoolman .......... G02B 21/362
850/10
6,901,941 B2 6/2005 Gershtein et al.
(Continued)

FOREIGN PATENT DOCUMENTS

CN 104939925 A 9/2015
JP 2005500096 A 1/2005
(Continued)

OTHER PUBLICATIONS

Mathies "Augmented reality comes to neurosurgery with tech developed by Leica" 2 pages, Aug. 6, 2016. http://www.digitaltrends.com/cool-tech/leica-captview-ar-brain-surther/#ixzz4KAChTpm8.
(Continued)

*Primary Examiner* — Carolyn A Pehlke
*Assistant Examiner* — Johnathan Maynard
(74) *Attorney, Agent, or Firm* — Harness, Dickey & Pierce, P.L.C.

(57) ABSTRACT

A system using images of a subject to assist in visualization of hidden portions of the subject is disclosed. The system may illustrate the images with a wearable display. The images may be displayed in an augmented or mixed reality manner.

27 Claims, 5 Drawing Sheets

(51) Int. Cl.
*A61B 34/00* (2016.01)
*A61B 90/50* (2016.01)
*A61B 90/00* (2016.01)
*A61B 5/00* (2006.01)
A61B 10/04 (2006.01)
A61B 17/00 (2006.01)
A61B 18/00 (2006.01)
A61B 90/14 (2016.01)

(52) U.S. Cl.
CPC .............. *A61B 34/25* (2016.02); *A61B 90/36* (2016.02); *A61B 90/37* (2016.02); *A61B 5/0071* (2013.01); *A61B 5/7445* (2013.01); *A61B 90/14* (2016.02); *A61B 2010/045* (2013.01); *A61B 2017/00199* (2013.01); *A61B 2017/00203* (2013.01); *A61B 2018/00446* (2013.01); *A61B 2034/107* (2016.02); *A61B 2034/2051* (2016.02); *A61B 2034/2055* (2016.02); *A61B 2034/2068* (2016.02); *A61B 2034/2072* (2016.02); *A61B 2090/365* (2016.02); *A61B 2090/367* (2016.02); *A61B 2090/368* (2016.02); *A61B 2090/374* (2016.02); *A61B 2090/3762* (2016.02); *A61B 2090/502* (2016.02); *A61B 2505/05* (2013.01); *A61B 2560/0475* (2013.01); *A61B 2576/026* (2013.01)

(58) Field of Classification Search
CPC ...... A61B 2090/502; A61B 2034/2072; A61B 2010/045; A61B 90/39; A61B 5/1114; A61B 5/746; A61B 5/0077; A61B 5/1127; A61B 5/1115; A61B 5/1128; A61B 5/0033; A61B 2090/366; A61B 2090/371; A61B 2090/373; A61B 2090/364; A61B 2034/101; A61B 2034/102; A61B 2034/104; A61B 2034/105; A61B 2034/2046; A61B 2034/2057; A61B 2034/2063; A61B 2034/2065; G02B 27/017; G02B 2027/0178; G16H 40/63
USPC ................................................ 600/424–425
See application file for complete search history.

(56) References Cited

U.S. PATENT DOCUMENTS

| | | | |
|---|---|---|---|
| 7,001,045 | B2 | 2/2006 | Gregerson et al. |
| 7,106,825 | B2 | 9/2006 | Gregerson et al. |
| 7,108,421 | B2 | 9/2006 | Gregerson et al. |
| 7,188,998 | B2 | 3/2007 | Gregerson et al. |
| 8,238,631 | B2 | 8/2012 | Hartmann et al. |
| 8,467,133 | B2 | 6/2013 | Miller |
| 8,600,478 | B2 | 12/2013 | Verard et al. |
| 8,644,907 | B2 | 2/2014 | Hartmann et al. |
| 8,670,816 | B2 * | 3/2014 | Green ................. A61B 17/221 600/424 |
| 8,842,893 | B2 | 9/2014 | Teichman et al. |
| 8,891,847 | B2 | 11/2014 | Helm et al. |
| 9,411,057 | B2 | 8/2016 | Helm et al. |
| 9,412,200 | B2 | 8/2016 | Helm et al. |
| 9,486,628 | B2 | 11/2016 | Christopherson et al. |
| 9,675,319 | B1 * | 6/2017 | Razzaque ............. A61B 6/037 |
| 9,807,860 | B2 | 10/2017 | Helm et al. |
| 9,889,299 | B2 | 2/2018 | Ni et al. |
| 10,639,104 | B1 | 5/2020 | Barral et al. |
| 2002/0075201 | A1 | 6/2002 | Sauer et al. |
| 2003/0117369 | A1 | 6/2003 | Spitzer et al. |
| 2003/0163038 | A1 | 8/2003 | Simon et al. |
| 2005/0085714 | A1 * | 4/2005 | Foley ................. A61B 17/8872 600/424 |
| 2005/0203367 | A1 * | 9/2005 | Ahmed .................. A61B 90/36 600/407 |
| 2005/0228270 | A1 | 10/2005 | Lloyd et al. |
| 2005/0289472 | A1 | 12/2005 | Morita et al. |
| 2007/0184422 | A1 | 8/2007 | Takahashi |
| 2009/0088634 | A1 | 4/2009 | Zhao et al. |
| 2009/0088830 | A1 * | 4/2009 | Mohamed ............ A61B 6/4423 623/1.11 |
| 2009/0326318 | A1 | 12/2009 | Tognaccini et al. |
| 2010/0228117 | A1 * | 9/2010 | Hartmann .............. A61B 5/064 600/426 |
| 2010/0290690 | A1 | 11/2010 | Hartmann et al. |
| 2012/0097178 | A1 * | 4/2012 | Helm ...................... A61B 6/032 378/62 |
| 2012/0099768 | A1 * | 4/2012 | Helm ....................... A61B 6/02 600/431 |
| 2012/0099772 | A1 | 4/2012 | Helm et al. |
| 2012/0250818 | A1 * | 10/2012 | Helm .................... A61B 6/4447 378/4 |
| 2012/0250822 | A1 | 10/2012 | Helm et al. |
| 2013/0060146 | A1 * | 3/2013 | Yang ..................... G01B 11/25 600/476 |
| 2013/0072787 | A1 | 3/2013 | Wallace et al. |
| 2013/0188848 | A1 | 7/2013 | Helm et al. |
| 2013/0237811 | A1 * | 9/2013 | Mihailescu .......... A61B 6/4405 600/407 |
| 2013/0267833 | A1 | 10/2013 | Schroeder |
| 2014/0002630 | A1 | 1/2014 | Yokota |
| 2014/0221819 | A1 | 8/2014 | Sarment |
| 2014/0275989 | A1 | 9/2014 | Jacobsen et al. |
| 2015/0005622 | A1 * | 1/2015 | Zhao ..................... G16H 40/67 382/103 |
| 2015/0363979 | A1 * | 12/2015 | Takano .............. G02B 27/0093 345/633 |
| 2016/0030131 | A1 | 2/2016 | Yang et al. |
| 2016/0030132 | A1 | 2/2016 | Cheung et al. |
| 2016/0191887 | A1 * | 6/2016 | Casas ..................... A61B 34/20 348/47 |
| 2016/0220324 | A1 * | 8/2016 | Tesar ...................... A61B 90/20 |
| 2016/0242623 | A1 * | 8/2016 | Pasini ..................... G06T 11/60 |
| 2016/0248994 | A1 | 8/2016 | Liu |
| 2016/0324580 | A1 * | 11/2016 | Esterberg ................ A61B 34/10 |
| 2017/0151432 | A1 | 6/2017 | Christopherson et al. |
| 2017/0202633 | A1 * | 7/2017 | Liu ........................ G16H 40/63 |
| 2018/0042681 | A1 * | 2/2018 | Jagga ..................... A61B 90/36 |
| 2018/0049622 | A1 | 2/2018 | Ryan et al. |
| 2018/0092698 | A1 | 4/2018 | Chopra et al. |
| 2018/0140362 | A1 * | 5/2018 | Cali ........................ A61B 34/20 |
| 2019/0083180 | A1 | 3/2019 | Ichiki |
| 2019/0099068 | A1 * | 4/2019 | Jessop ..................... A61B 1/045 |

FOREIGN PATENT DOCUMENTS

| | | |
|---|---|---|
| JP | 200918184 A | 1/2009 |
| JP | 2009524149 A | 6/2009 |
| JP | 2016503676 A | 2/2016 |
| JP | 2016512658 A | 4/2016 |
| JP | 2016158911 A | 9/2016 |
| WO | 2012075155 A2 | 6/2012 |

OTHER PUBLICATIONS

Straka "A.R. Enhanced Navigated Biopsy Storyboard" Medtronic Neurosurgery, Feb. 2016, 11 pages.
Invitation to Pay Additional Fees dated Nov. 20, 2017 in corresponding International Application No. PCT/US2017/052411.
International Search Report and Written Opinion dated Jan. 2, 2018 in corresponding International Application No. PCT/US2017/052411.
NewTom Cone Beam 3d Imaging product brochure, 12 pages, 2017.
ODG Smartglasses 9 product brochure, 2 pages, 2018.
U.S. Appl. No. 16/210,647, filed Dec. 5, 2018, Godwin et al.
U.S. Appl. No. 16/210,669, filed Dec. 5, 2018, Godwin et al.
International Preliminary Report on Patentability dated Apr. 4, 2019 in corresponding/related International Application No. PCT/US2017/052411.

(56) References Cited

OTHER PUBLICATIONS

International Search Report and Written Opinion dated Feb. 22, 2019 in corresponding/related International Application No. PCT/US2018/064280.
International Preliminary Report on Patentability dated Jun. 18, 2020 in corresponding/related International Application No. PCT/US2018/064280.
Japanese Office Action (with English translation) regarding Japanese Application No. 201951598.7, dated Jul. 5, 2021.
Office Action regarding Korean Patent Application No. 10-2019-7010899, dated Oct. 6, 2021.
Chinese Office Action (with English translation) regarding Chinese Application No. 201180012267.3, dated Nov. 1, 2021.
European Office Action regarding 18822230.1, dated Nov. 8, 2022.
Korean Office Action regarding Patent Application No. 1020197010899, dated Jun. 7, 2022.
European Office Action corresponding to EP177780640, dated Dec. 23, 2022.
Examination Report corresponding to European Application No. 18822230.1, dated Aug. 9, 2023 (5 pp).

* cited by examiner

SYSTEM FOR GUIDED PROCEDURES

FIELD

The subject disclosure relates to an image viewing system, and particularly relates to a system to view images displayed relative to or superimposed on a real object to which the image relates.

BACKGROUND

This section provides background information related to the present disclosure which is not necessarily prior art.

During a procedure, a computer-aided surgical (CAS) system may be used to assist a user, such as a surgeon. Procedures may include surgical procedures such as tumor resection and/or ablation of tissue in a brain. The CAS system may also be referred to as a surgical navigation system and allows the display of an image of a portion of a patient on a display. For example, a surgical navigation system may include the Stealth Station® 57® Surgical Navigation System, sold by Medtronic Navigation, Inc., having a place of business in Colorado, USA. The surgical navigation system allows the user to register image space to real or patient space using a registration technique, such as identifying fiducial points on the patient and in an image. The registration may apply to images displayed on a screen positioned away from the patient. The displays may be monitors, such as cathode ray tube (CRT) monitors and/or flat panel monitors including backlit displays such as a video monitors sold by ViewSonic Corporation. The display is positioned away from the patient such that it may be difficult for the user to view the image on the display and the patient simultaneously, including at least in the same real space.

SUMMARY

This section provides a general summary of the disclosure, and is not a comprehensive disclosure of its full scope or all of its features.

According to various embodiments, a surgical navigation system includes a holographic or augmented reality display. The augmented reality display may include a mixed reality display or device, as discussed herein. The mixed reality (MR) device may be mounted, such as worn, by one or more users in a selected real space. The MR device allows the user to view real space and objects along with generated images (e.g. icons) displayed relative to or superimposed on the real objects in the real space. The MR device may also include features configured to allow the MR device to identify and remember a physical location of the MR device in the real space.

The MR device may include a display operable to be configured to display an image superimposed on a real or subject space. The subject space may include an animate or inanimate subject. For example, an animate subject may include a human patient or an animal patient, while an inanimate subject may include a mechanical or electrical system. In various embodiments, a human subject may be experiencing a surgical procedure and the MR device may be used to illustrate or display an image of the patient superimposed on the patient. In a procedure on an inanimate object, the MR device may be used to superimpose an image of internal component of a system that is covered by an external layer or casing.

In various embodiments, the MR device may devices configured to display images, as discussed herein, that are viewable in combination with real world objects and features by a user. Exemplary devices that are able to display images for viewing by a user include the Holo Lens® by Microsoft Corporation, having a place of business in Washington, USA and the Meta 2® digital display sold by Meta Company, having a place of business in California, USA, and other appropriate mixed reality display devices. Generally, the MR device, which may include various augmented reality display devices, is a head-mounted display device that is directly viewable by the user and may be used to superimpose an image or icons on a real space. As discussed herein, the MR device may be used to display selected icons and images for a selected procedure.

In various embodiments, the MR device may also be referred to as or include elements of an augmented reality system. In the mixed reality system, a viewer may view both the real world or real space (e.g., patient space) and further view a display superimposed on the real world. For example, a user may view both (1) the real world, through a display portion of the MR device that is transparent, and (2) displayed on the display portion opaque or semi-opaque elements (e.g. projections or embedded liquid crystal displays) that may also be viewed by the user. In various embodiments, the user may view both the real world and the displayed elements simultaneously. The mixed reality system, as discussed further herein, may allow registration of pre-acquired images to display that are registered to the subject when viewed through the MR device. Therefore, a user may view both the real space and the image space simultaneously and have the image space registered to the real space for viewing of various features and items identified in the image space as if they existed in the real space.

Further, the augmented or mixed reality system allows for the user to view other images or icons superimposed on the real space and/or the image space. The icons can be based upon planned or navigated positions of an instrument relative to the subject as the icons are displayed with the augmented reality device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
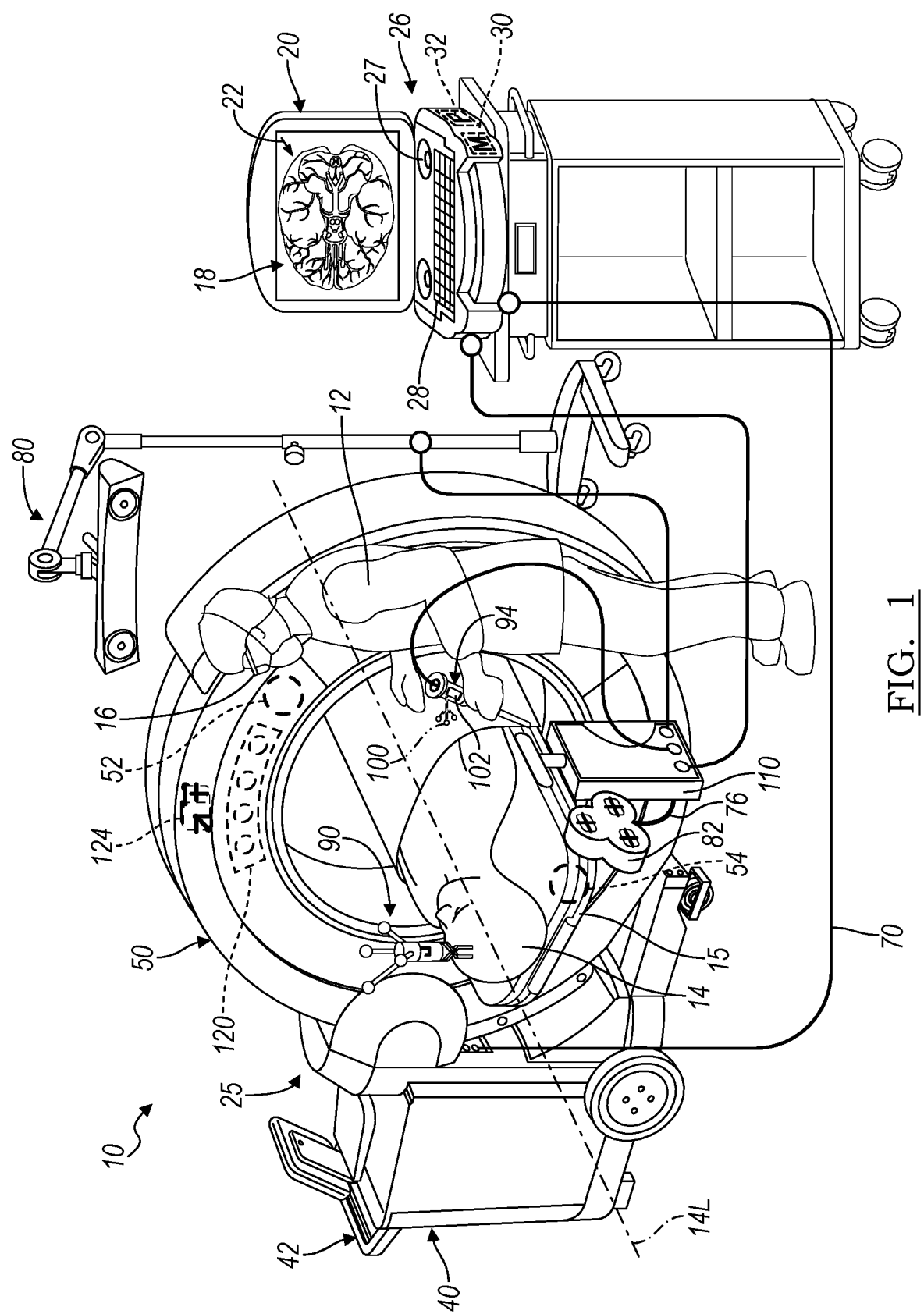
FIG. 1 is a schematic view of a surgical navigation system including a MR device.

Example embodiments will now be described more fully with reference to the accompanying drawings.

According to various embodiments, an operating room or theater 10 may be used by a user 12, such as the surgeon, to perform a selected procedure on a subject, such as a human subject 14. As noted above, however, the subject 14 need not be a human subject and the procedure need not be a surgical procedure. According to various embodiments, the subject 14 may be an inanimate object, such as an electrical or mechanical system within a housing. The various components, including the augmented or mixed reality system as discussed herein, may be used to view an exterior of the subject 14 along with various components interior to the subject 14 or within a housing of the subject 14 for performing a procedure.

In the operating room 10, various components may be provided to assist the user 12 in performing a procedure. According to various embodiments, a viewing system may include a mixed reality display device or system 16. The mixed reality display device 16 may be a wearable mixed reality display device, such as a head mounted device similar to glasses or goggles. The mixed reality device 16 may also be a device positioned near or adjacent the user 12 and/or moveable with the user 12. The mixed reality display device 16 may be used by the user 12 to view the subject 14 and other information, such as an image as a MR image 18a (illustrated in FIGS. 2 and 2A) and/or other information of the subject 14 and/or icons 22 related to various portions relative to the subject 14. Further, an external or non-mixed reality display device 20 may be also used to display the image as an image 18 with the display 20. The MR image 18a may be viewable with the MR display 16 to be viewed by the user 12, as discussed further herein.

As discussed herein, the viewable images 18, 18a may be based upon image data acquired with an imaging system, such as an imaging system 25. It is understood that the images 18, 18a may be registered to the subject, as also discussed herein, and be based on the image data from the imaging system 25. As discussed herein, the image 18 may generally refer to an image based on the image data and discussion specifically of the MR image 18a is the image viewed with the MR device 16.

The Imaging system 25 can include imaging systems, as discussed herein, that acquire image data (e.g., based upon x-ray transmission through the subject 14) to generate the images 18. It is also understood that other image data may also be used to generate the images 18 for viewing by the display device 20 or the MR image 18a for viewing with the MR display 16. Further, one or more icons 22 may be illustrated on the display device 20 and the MR display 16. The icon 22 may be superimposed on the image 18 on the display device 20, according to various embodiments. Further, the icon 22 may be displayed with the MR device 16 either superimposed on the MR image 18a and/or superimposed on the subject 14. As discussed herein, the icon 22 may be displayed on the MR device 16 as a mixed reality image viewable by the user 12 such that the icon 22 appears to be directly imposed on the subject 14.

With continuing reference to FIG. 1, to assist in performing the procedure, the user 12 can use the imaging system 25 to acquire image data of the subject 14 to allow a selected system to generate or create images to assist in performing the procedure. A model (such as a three-dimensional (3D) image) can be generated using the image data and displayed as the MR image 18a on the MR display 16 and/or the image 18 on the display device 20. The display device 20 can be part of and/or connected to a processor system 26 that includes an input device 28, such as a physical or oral input devices (e.g. keyboard, touchscreen, speech control), a memory system 30 (e.g. spinning hard disk, solid state memory devices, random-access memory) which may generally include non-transient memory systems, and a processor 32. The processor 32 may include one or more processors or microprocessors incorporated with the processing system 26. Communication portions, such as electrical wire connections or wireless transmission connections are understood to be provided between the various components of the processor system 26 (e.g. the processor 32 and the display device 20 for data communication to allow driving the display device 20 to display or illustrate the image 18) and/or various other components within the operating room 10, as discussed herein.

The imaging system 25 can include an O-Arm® imaging system sold by Medtronic Navigation, Inc. having a place of business in Louisville, Colo., USA. The imaging system 25, including the O-Arm® imaging system, or other appropriate imaging systems may be in use during a selected procedure, such as the imaging system described in U.S. Pat. Nos. 9,412,200; 7,188,998, 7,108,421; 7,106,825; 7,001,045; and 6,940,941 and U.S. Patent App. Pubs. 2012/0250822; 2012/0099772; and 2010/0290690, all incorporated herein by reference.

The imaging system 25, when, for example, including the O-Arm® imaging system, may include a mobile cart 40 that includes a control panel or system 42 and an imaging gantry 50 in which is positioned a source unit 52 and a detector 54. The control system 42 may include various components, such as a processor (e.g. such as those discussed above), a memory, and various human input systems. Therefore, the control system 42 may be operated or include instructions for moving at least the gantry 50, the source 52, and the detector 54 to acquire image data of the subject 14. Further, the control system 42 may be used and/or operated to move the imaging system 25 from one location to another, such as within a hospital or other care giving facility.

The gantry 50 may be O-shaped or toroid shaped, wherein the gantry is substantially annular and includes walls that form a volume in which the source unit 52 and detector 54 may move. The mobile cart 40 can be moved from one operating theater to another and the gantry 50 can move relative to the cart 40, as discussed further herein. This allows the imaging system 25 to be mobile and moveable relative to the subject 14 thus allowing it to be used in multiple locations and with multiple procedures without requiring a capital expenditure or space dedicated to a fixed imaging system. The control system 42 may include a processor such as a general purpose processor or a specific application processor and a memory system (e.g. a non-transitory memory such as a spinning disk or solid state non-volatile memory). For example, the memory system may include instructions to be executed by the processor to perform functions and determine results, as discussed herein.

The source unit 52 may be an x-ray emitter that can emit x-rays through the patient 14 to be detected by the detector 54. The gantry 50 may move relative to a longitudinal axis 14L of the patient 14 and the source 52 and detector 54 may rotate around the axis 14L. The imaging device 25 can be precisely controlled to move the source/detector 52/54 relative to the patient 14 to generate precise image data of the patient 14. The imaging device 25 can also be connected with the processor system 26 via selected connections such as a connection 70 which can include a wired or wireless connection or physical media transfer from the imaging system 25 to the processor system 26. Thus, image data collected with the imaging system 25 can be transferred to the processing system 26 for navigation, display, reconstruction, etc. as discussed herein.

It is understood that the imaging system 25 may be any appropriate imaging system and need not be the O-Arm® imaging system disclosed above. Other appropriate imaging systems may include a magnetic resonance imaging (MRI), functional MRI, diffusion tensor imaging (DTI), a computed tomography (CT) scanner, positron emission tomography (PET) scan, stereo camera, etc. Any appropriate imaging system may be used to acquire image data of the subject 14. Further, the imaging system 25 may be present in the operating room 10 or may be provided outside of the operating room 10 to acquire image data separate from the area in which the procedure is being performed by the user 12. Thus, the image data may be pre-procedure data, intra-procedure image data (i.e. acquired before completing a procedure), or post-procedure image data.

In a navigated procedure, a localizer and/or digitizer, including either or both of an optical localizer 80 and an electromagnetic localizer 82 can be used to generate a field and/or receive and/or send a signal within a navigation domain relative to the patient 14. The navigated space or navigation domain relative to the patient 14 is patient or real space that is registered to an image space of the image 18. Registration is based on a correlation, as understood in the art, to allow registration of a navigation space defined within the navigational domain and an image space defined by the image 18. A patient tracker or dynamic reference frame (DRF) 90 can be connected to the patient 14 to allow for a dynamic registration and maintenance of registration of the patient 14 to the image 18.

The patient tracking device or dynamic registration device 90 and an instrument 94 can then be tracked relative to the patient 14 to allow for a navigated procedure. The instrument 94 can include a tracking device, such as an optical tracking device 100 and/or an electromagnetic tracking device 102 to allow for tracking of the instrument 94 with either or both of the optical localizer 80 or the electromagnetic localizer 82. A communication system may be provided between the instrument 94 and the processor system 26 which may be with or through a navigation/probe interface device 110. Also, the one or more localizers 80, 82 may communicate through the navigation/probe interface device 110 with the processor system 26. The processor system 26, therefore, may operate in cooperation with the other tracking components as a navigation system to incorporate tracked locations of the patient 14 and/or the instrument 94 based on the various tracking devices 90, 100, 102. The tracked locations may be illustrated as tracked locations on the image 18 and/or the patient 14. It is understood that the communications may be wired, wireless, physical media transmission or movement, or any other appropriate communication. Nevertheless, the appropriate communication systems can be provided with the respective localizers 80, 82 to allow for tracking of the instrument 94 relative to the patient 14 to allow for illustration of a tracked location of the instrument 94 relative to the image 18 and/or the patient 14 for performing a procedure.

One skilled in the art will understand that the instrument 94 may be any appropriate instrument, implant, or probe. For example, the instrument 94 may include a ventricular or vascular stent, spinal implant, neurological stent or stimulator, ablation device, or the like. The instrument 94 can be an interventional instrument or can include or be an implantable device. Tracking the instrument 94 allows for determining and/or viewing a location (including x, y, z position and orientation) of the instrument 94 relative to the patient 14 and/or the registered image 18 (e.g. displaying an icon representing the instrument) without direct viewing of the instrument 94 within the patient 14.

Further, the imaging system 25 may be tracked with one or more of the localizers 80, 82. For example, the gantry 50 can include an optical tracking device 120 or an electromagnetic tracking device 124 to be tracked with the respective optical localizer 80 or electromagnetic localizer 82. Accordingly, the imaging device 25 can be tracked relative to the patient 14 as can the instrument 94 to allow for initial registration, automatic registration, or continued registration of the patient 14 relative to the image 18. Further, the imaging system 25 may "know" the location of the imaging portions (such as the detector) when an image is acquired to allow it to be registered to the patient 14 when the patient 14 remains in the same location or is tracked after the image acquisition. Upon registration and tracking of the instrument 94, the icon 22 may be displayed relative to, including superimposed on, the image 18 and/or the patient 14.

Figure 2:
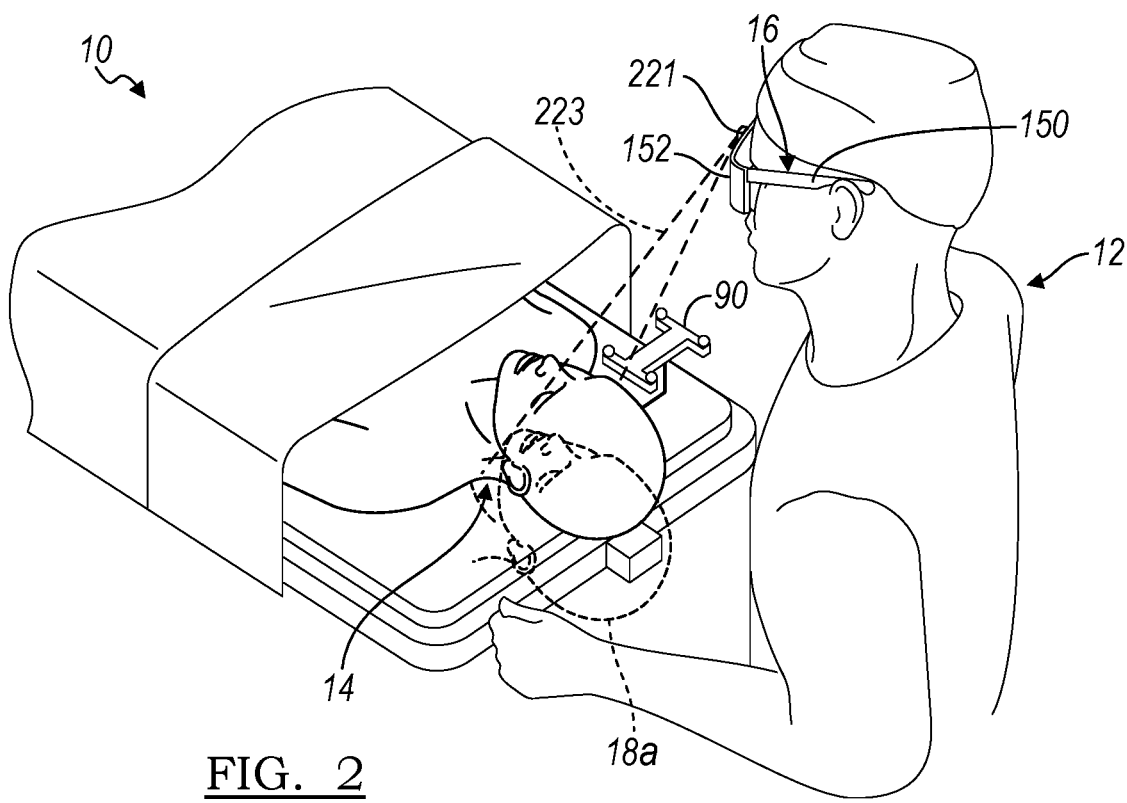
FIG. 2 is a schematic view of a user with a MR device viewing an image and a real object.
Figure 2A:
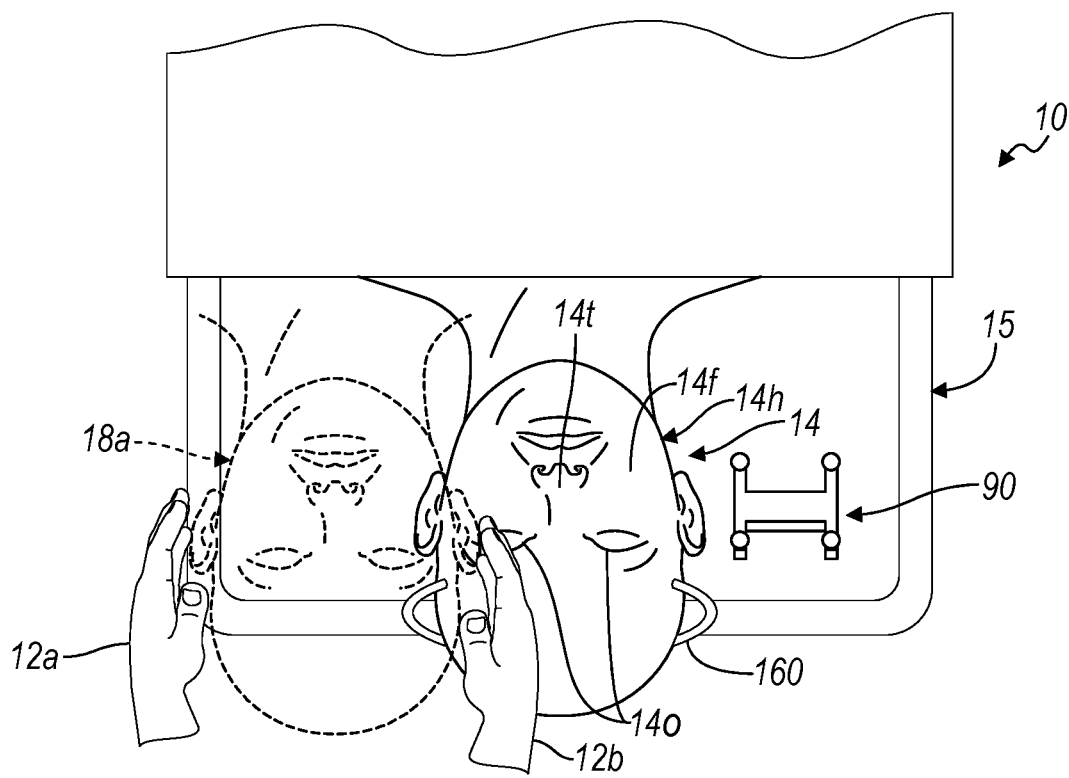
FIG. 2A is a user's perspective view using the MR device to view a real object and an image, according to various embodiments.
Figure 3:
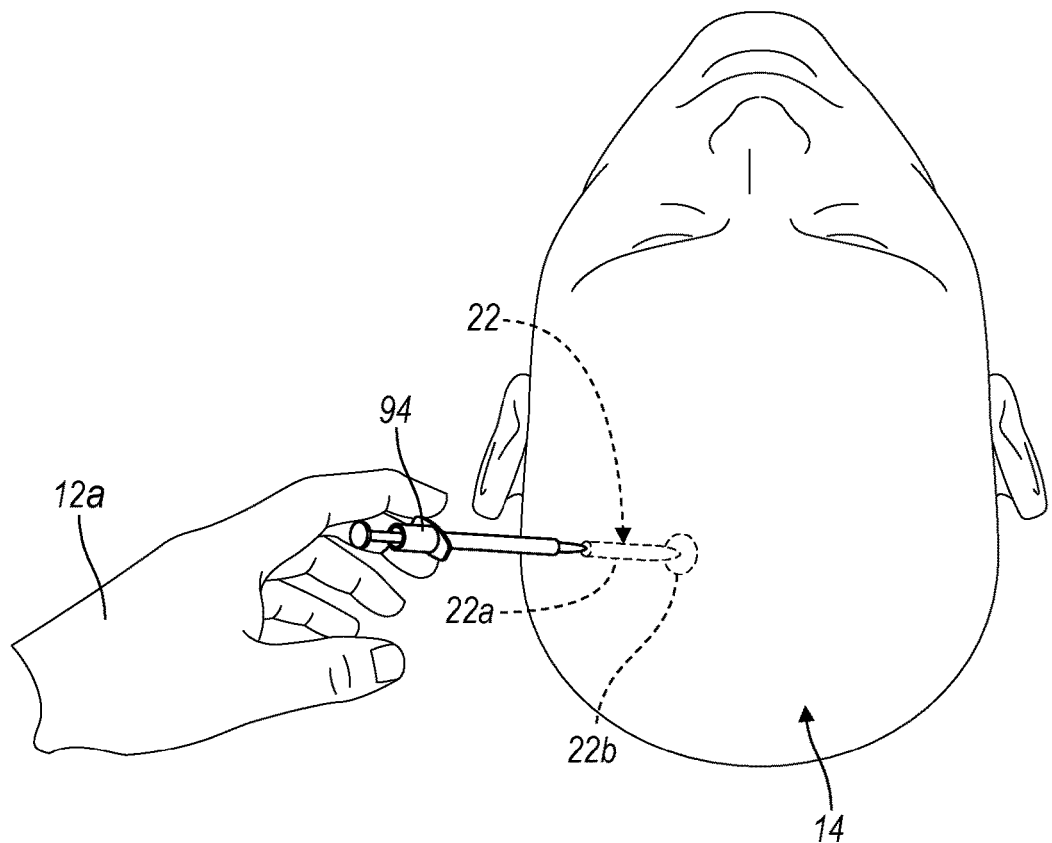
FIG. 3 is a user's perspective view using the MR device to view a real object and an image, according to various embodiments.

In various embodiments, registration and navigated procedures, as discussed herein, may include those as disclosed in U.S. Pat. No. 8,238,631, incorporated herein by reference. Tracking systems, including trackable instruments and registration processes, are also disclosed in U.S. Pat. Nos. 8,644,907; 8,600,478; 8,842,893; 8,891,847; U.S. Patent App. Pub. No. 2013/0188848; and U.S. Patent App. Pub. No. 2014/0275989; all incorporated herein by reference. Registration performs a correlation of x, y, z positions in real or patient space and correlates them to x, y, z positions in the image space (i.e. x, y, z, positions of pixels or voxels in the image). Tracked positions of the instrument 94 may then be illustrated as the icon 22 on the display 20, such as superimposed on the image 18. In various embodiments, however, the registration may also allow the MR image 18a to be superimposed on the patient 14 in a mixed reality view with the MR display 16. Thus, the user 12 would see both the MR image 18a and the patient 14, as illustrated in FIG. 2 and FIG. 2A. Moreover, the icon 22 may be displayed with the MR display 16 with the MR image 18a, as illustrated in FIG. 2 or without the MR image 18a (e.g. superimposed on the patient 14) as illustrated in FIG. 3.

Prior to registration, or after registration if selected by the user 12, the MR image 18a may be viewed separately from the subject 14. For example, the user 12 may instruct the system 26 to display an image of the subject 14 for planning a procedure, such as tumor resection. When viewing the image without the subject 14 present the user 12 may identify all or part of a tumor in the image. The processing system 26 may segment the image data to identify boundaries of the tumor. The user 12 and/or other users alone or in combination with planning systems may also define or select trajectories for an instrument, entry locations, annotations of the image 18 and/or the subject 14 as viewed with the MR device 16, etc.

All of the planning may be stored as a surgical plan in the memory 30. At a selected time, the user 12 may instruct the processor system 26 to recall the surgical plan and display at least parts of the surgical plan (i.e. a trajectory, tumor segmentation, implant design and/or sizing, instrument selection, procedure location, etc.) with the MR device 16. The surgical plan may be displayed super imposed on the subject 14 with or without other images. In addition, as discussed herein, various internal structures may be illustrated as icons, segmented portions of the MR image 18a, etc. For example, an icon 22b (FIG. 3) representing a tumor may be displayed with the MR device 16 which may be internal to the subject 14 and not directly viewable by the user 12.

With initial reference to FIG. 2 and FIG. 2A, the user 12 may register the MR image 18a to the patient 14 in the operating theater 10 once the patient 14 is positioned within the operating theater 10. The user 12 when using the MR device 16 may, however, view images without the patient 14 being present. Various planning and confirming procedures may be performed before the user 12 beginning a procedure with the patient 14 present. Preplanning may be saved in the memory for recall at a later time, including planned entry points, identified disease regions (e.g. tumor), instrument trajectories, and the like.

In various embodiments, the MR device 16 is a wearable MR device and the user 12 wears the MR device 16. As a wearable MR device, the MR device 16 may include a head mounting or wearing portion 150 and a transparent or semi-transparent viewing portion or display 152. The viewing portion 152 may include a transparent or semi-transparent portion (e.g. a lens or a screen) through which the user 12 may view real space, including the patient 14. The viewing portion 152 may include the transparent or semi-transparent viewing portion that includes a liquid crystal portion that may be made opaque to display the MR image 18a and/or other features (e.g. the icon 22). When transparent or semi-transparent the viewing portion 152 allows the user 12 to view the subject 14 and other real world objects and features. The viewing portion 152 may be driven by signals from the processing system 26.

The viewing portion 152, however, may also include various features (such as one-way view screens) that allow an image to be displayed in the field of view of the user 12. Therefore, the user 12 may view both the real patient 14 and the MR image 18a substantially simultaneously. The user 12 may view the patient 14 and the MR image 18a, as illustrated in FIG. 2A. FIG. 2 may illustrate a representation of a second user (e.g., a nurse in the operating room) also wearing the MR device 16 and viewing the user 12, the patient 14, and the MR image 18a. FIG. 2A illustrates a field of view of the user 12 viewing through the MR display 16 to view the patient 14 and the MR image 18a. As illustrated in FIG. 2A, however, the MR image 18a may not initially be registered to the patient 14 as the MR image 18a is offset and not overlaid on the patient 14. During a registration process, however, the user 12 may appear to grasp the MR image 18a with hands 12a, 12b of the user 12 to move the MR image 18a to assist in performing registration of the image space defined by the image 18 to the patient space defined by the patient 14. The DRF 90 may be attached to the patient 14 directly, such as being attached to the patient 14 or may be attached to a clamp 160 that fixes the patient's head 14h to an operating table 15 in the operating theater 10.

In a registration process, either or both visual or audio cues are made to the user 12 to assist in the registration. As discussed above, the MR display 16 may display any appropriate information to the user 12, such as icons or other indicia (e.g., numbers, words, and the like) to convey information from the processor system 26. As discussed above, the MR display 16 is in communication with the processor system 26 to assist in navigation and the display of information relative to the patient 14, such as the MR image 18a. As noted above, the image data may be acquired with the imaging device 25 and transmitted to the processing system 26 and/or stored on the memory 30, or other appropriate memory, and recalled to be displayed on the MR display 16. Further information, such as navigation information, may also be displayed on the MR display 16 based upon processes of the processor system 26.

Figure 4:
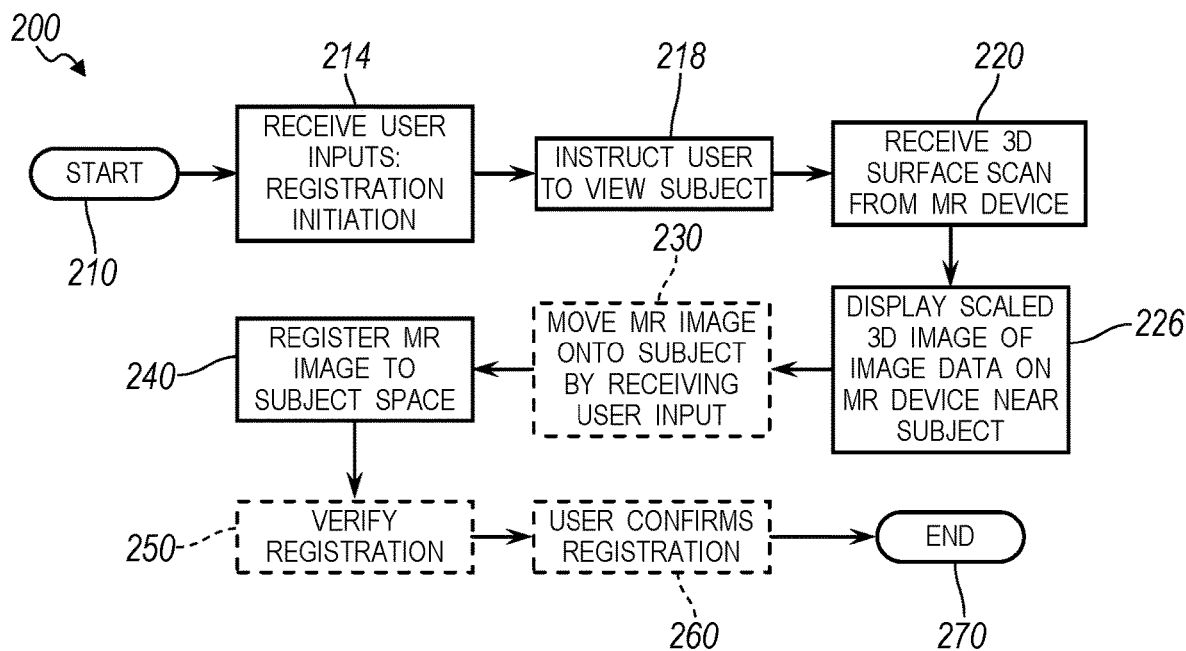
FIG. 4 is a flowchart illustrating a method of registration of an image space to a real space.

To perform registration of the image space to the patient space to perform or assist in navigating a procedure relative to the patient 14, a registration process may initiate. With continued reference to FIG. 2A and additional reference to FIG. 4, a registration flowchart 200 is illustrated. The registration process may begin in START block 210 of the flowchart process 200. The user 12 then initiates the registration process in block 214. The initiation of the registration process may include the user 12 using the input 28. As noted above, the input 28 may include any appropriate input, including oral input. Therefore, the user 12 may initiate registration by providing an oral command (e.g., "navigation-start registration"). The processor system 26 may receive the input and initiate execution of instructions to register the image space of the image 18 to the patient space of the patient 14.

In the method 200, the processor system 26 may instruct the user to view the subject in block 218. The instruction may be displayed on the MR display 16 or may otherwise be provided to the user 12, such as with an oral or auditory output from the processor system 26. Therefore, it is understood that the processor system 26 may also include an output in addition to the display 20 or the display 16, such as a speaker 27 (see FIG. 1).

Once instructed, the user 12 may view the subject 14 with the MR display 16 appropriately positioned for use by the user 12. In various embodiments, appropriate placement of the MR display 16 may be placing the MR display 16 on the user's head similar to glasses. As illustrated in FIGS. 1 and 2, the MR display 16 may be worn by the user 12 in any appropriate manner that fixes the display portion 152 of the MR display 16 in the user's field of view. The processing system 26 may then receive a 3D surface scan from the MR display 16 in block 220.

The 3-D surface scan received in block 220 may be achieved with a scanning or range finding portion 221 of the MR display 16. Various scanning or range finding systems may include laser scanners (e.g. lidar), radar scanners, optical scanners, ultrasound, stereoscopic cameras, or other range finding systems configured to obtain a surface scan of the subject to define one or more points (e.g. x, y, and z three-dimensional coordinates) of portions of the subject 14 and other objects in real space. With reference to FIG. 2, the range finding portion may scan the subject in a scan field 223. For example, a laser (e.g. an IR laser) may scan the surface of the subject 14 to identify points in real or subject space to correlate to pixels or voxels in the image 18 for registration, as discussed herein.

The user 12 in viewing the patient 14 while wearing the MR display 16 positions the MR display 16 in an appropriate location such that the 3D scanning system of the MR display 16 can properly scan the patient 14. In scanning the patient 14, a point cloud may be created of the patient 14. For example, as illustrated in FIG. 2 and FIG. 2A, a surface scan of a face 14f of the patient 14 may be made. The face 14f may include a scan of a nose tip 14t, a scan of a patient's orbits 14o, and other anatomical features of the patient 14. In addition, points between the identified anatomical features may also be scanned in the point cloud. These points received as 3-D surface scans by the MR display 16 can be transferred to the processing system 26.

Subsequent to or substantially at the same time as initiating or after receiving the 3D surface scan from block 220, the processing system 26 displays a scaled 3D image of the image data on the MR device 16 near the subject 14. Returning reference to FIG. 2A, the MR image 18a may be displayed near or partially overlapping the subject 14 when viewed by the user 12 through the MR device 16. As illustrated in FIG. 2A the MR image 18a may be scaled relative to the patient 14. For example, the surface scan data from block 220 may identify a size of the patient 14 in the real space. Therefore the MR image 18a may be displayed as a 1:1 scale of the patient 14. In other words, the MR image 18a may be a three-dimensional rendering based upon the image data acquired with the imaging system 25 and may be scaled to the patient 14 based upon the received surface scan data from block 220. The MR image 18a may be, therefore, surface matched to the subject 14. Regardless, the MR image 18a may be displayed in the mixed reality space as viewed through the MR device 16 by the user 12 as the user 12 is able to view both a patient 14 and the MR image 18a in the apparent same space.

In viewing both the MR image 18a and the patient 14 in the same space, the user 12 is able to proceed and understand both the position of the patient 14 and a displayed or projected position of the MR image 18a. Although it is understood that the MR image 18a may only be viewable through the MR device 16 by the user 12, it is understood that the user 12 perceives that the MR image 18a is in the same space as the patient 14. This allows the user 12 to view only the subject 14 and understand and perceive information from the image data, planning, and/or tracking of instruments, as discussed herein. This may be an alternative to viewing the subject 14 and the display 20 positioned away from the subject 14. It is further understood that other users, such as a surgical nurse, may have a device similar or identical to the MR device 16 and may also perceive the MR image 18a, the patient 14, and the user 12. Further, it is also understood that the image 18 may be displayed on the display 20 if selected.

In displaying the image 18 as a three-dimensional rendering in the mixed reality, referred to herein as the MR image 18a, the user 12 is able to view the MR image 18a relative to the patient 14. Further, the user 12 is able to view other real world features and objects, such as hands 12a, 12b, of the user 12. Therefore, the user 12 may appear to grasp the MR image 18a. In attempting to grasp or appearing to grasp the MR image 18a, the user 12 may move the MR image 18a. The MR image 18a may move based upon input from the MR device 16 to the processing system 26. As discussed above, the MR device 16 may include features to identify and determine real world positions relative to the MR device 16. Therefore, the hands 12a and 12b of the user 12 may be identified in the real world space and the processing system 26 may understand the position of the hands 12a and/or 12b as providing input to the processor system 26. It will be understood, however, that the user 12 may identify or command the system to understand that the hands 12a, 12b are to be inputs or to provide input to the processing system 26. For example, the user 12 may provide a command through the user input 28 (e.g., an oral or physical input). For example, the user 12 may provide an oral command such as "receive hand input" so that the processor system 26 understands to identify and receive an input from the hands 12a, 12b, in manipulating the MR image 18a.

Regardless, the user 12 may move the MR image 18a in the mixed reality space substantially intuitively. That is, the user 12 may appear to grasp and move the MR image 18a as if the MR image 18a were a real world feature, such as patient 14. The user 12 therefore may intuitively understand the movement and position of the MR image 18a in the real world space.

The MR image 18a may include various features, such as handles, tabs, and the like that are projected or included in the MR image 18a that may also be touched to specifically identify to the processor system 26, through known locations of the hands 12a, 12b relative to the MR image 18a, that manipulation of the MR image 18a is to be initiated. It is understood that the user's hands 12a, 12b and/or objects manipulated by the user 12 may be used to provide inputs to the MR device 16 and/or the processing system 26. Further, the range are finding system 221 may be configured to track the user 12 and the hands 12a, 12b relative to the subject 14.

Therefore, the user 12 may move the MR image 18a for various purposes. For example, the user 12 may move the MR image 18a to view different features of the MR image. As noted above the MR image 18a is a three-dimensional rendering of the image data, such as of the subject 14. Therefore, the user 12 may attempt to view the MR image 18a in various manners and orientations relative to the user's viewpoint to assist in various procedures, such as planning a procedure, confirming planning of a procedure, or registration of the MR image 18a to the patient 14. The user 12 may also move the MR image 18a away from the subject 14 for planning (e.g. before performing any invasive procedures on the subject 14).

The MR image 18a may then be moved on to the subject 14, also as noted above by manipulating the MR image 18a by the user 12, to assist in or initiate registration. The moving of the MR image 18a onto the subject 14 may assist in moving or initiating registration of the MR image 18a onto the subject 14 by identifying at least a rough or starting point for registration. As is generally understood by one skilled in the art, the registration of image data defining image space to a real space or subject space may be initiated by identifying one or more points that are in the image space and the subject space. By moving the MR image 18a onto or near the subject 14, the user 12 may assist in identifying various points in the MR image 18a that are substantially similar to points on the subject 14. For example the user 12 may manipulate and move the MR image 18a to substantially place the point of the nose in the MR image 18a and the orbits in the MR image 18a onto the nose tip 14t and the orbits 14o on the patient 14. The moving of the MR image 18a may be optional by the user in block 230. Moving of the MR image may not be required for registering the MR image 18a to the subject space defined by the subject 14. Further, it will be understood that the MR image 18a may be moved for purposes other than registration. Therefore, it is understood that moving the MR image in block 230 is optional.

The processor system 26 may register the MR image 18a to subject space in block 240. Registration of the MR image 18a to the subject space defined by the subject 14 may be based upon various existing algorithms and processes that register image space to subject space. As is generally understood in the art, for example, a user or processor system may identify fiducial points in image data and define similar or identical points on the subject 14, such as with the instrument 94, which is tracked with the tracking system including the localizer 80, 82. The registration process then may create a point cloud based upon pixels or voxels in the image data and the fiducial points identified on the subject 14 to perform a surface matching between the patient 14 and the image data and compute or generate a transformation, including a rigid body transformation, which maps the coordinates of the pixels or voxels in the MR image 18*a* to the three-dimensional x, y and z positions in the real space defined by and relative to the patient 14. The transformation may consist of rotation and translation operations to match the point cloud of the image data to the point cloud defined in the real space.

The point cloud defined by the patient 14 may be based upon the received 3D surface scan in block 220. The image data used to generate the MR image 18*a* defines the image space and the point cloud based upon the position of the pixels and voxels therein. Therefore, the received 3D surface scan from block 220 and the determined location of the pixels and voxels in the image data allow for registration of the MR image 18*a* to the patient 14.

Figure 5:
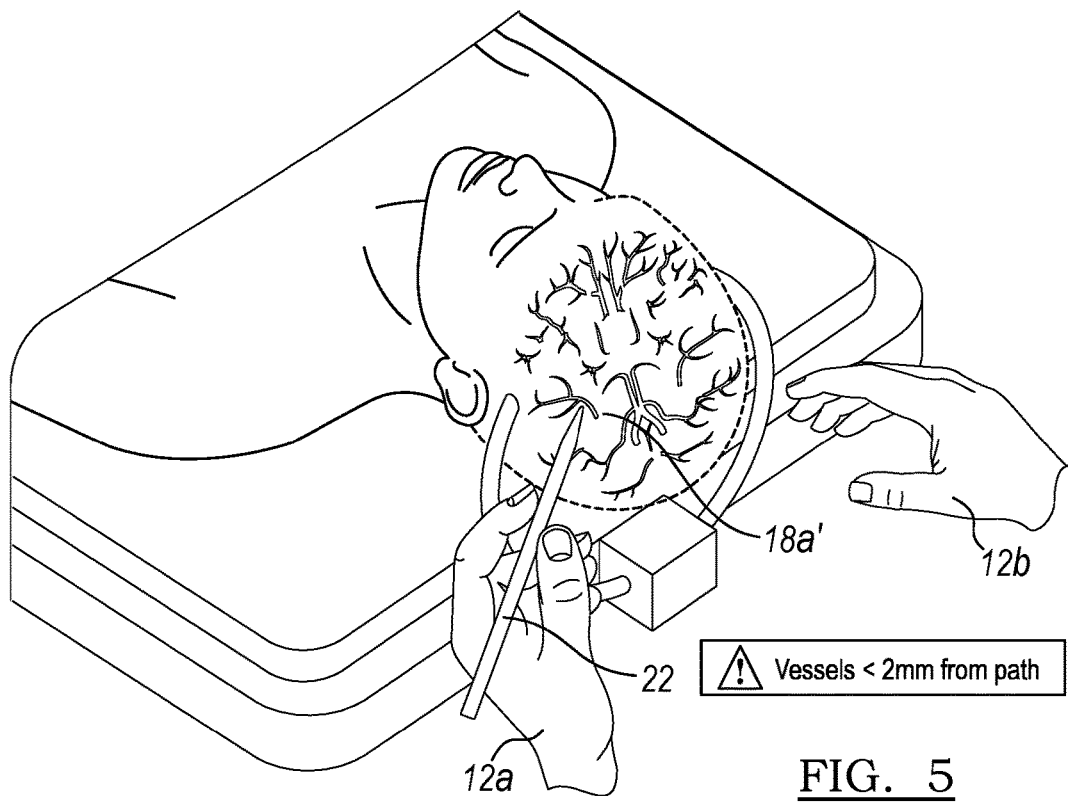
FIG. 5 is a user's perspective view using the MR device to view a real object and an image, according to various embodiments.

With brief reference to FIG. 5, the perceived view through the MR device 16 by the user 12 may allow the user 12 to view the user's hands 12*a*, 12*b* and one or more icons 22 and also the MR image 18*a* and/or portions based on the MR image 18*a* which may or may not be registered to the patient 14. As illustrated in FIG. 5, the registration of the image data to the patient 14 may allow for viewing of a substantially opaque MR image 18*a'* that is registered on the patient 14 and superimposed on the patient 14 when viewed through the MR device 16. As specifically illustrated in FIG. 5, the opaque MR image 18*a'* may include identification and illustration of blood vessels or other selected anatomical features. The registration, however, allows for superimposing of the opaque MR image 18*a'*, or other appropriate MR images, onto the patient 14 in the field of view of the user 12 with the MR device 16.

Also, the registration may include identification or viewing of the DRF 90 and/or surface scan of the DRF 90 relative to the subject 14. As discussed above, the tracking systems, including the localizers 80, 82, may be used to track instruments, such as the instrument 94. Therefore, the registration of the MR image 18*a* to the patient 14 may include an identification or determination of the registration relative to the DRF 90. Therefore a tracked location of the instrument 94 relative to the patient 14 may be displayed on the MR image 18*a* such as with the icon 22, as discussed further herein.

Returning reference to FIG. 4, after registration in block 240, a verification step may optionally occur in block 250 to verify registration. In verifying the registration accuracy, a holographic visualization or other visualization technique may be used. For example, a point cloud, wireframe, texture map, or other image may be projected onto the patient 14 with the MR device 16. The user 12 may view the patient 14 and, for example, a wireframe superimposed on the patient 14 without the MR image 18*a*. The wireframe may include several points, such as points at the nose tip 14*t* and orbits 14*o* and may have lines interconnecting the points. It is understood that a plurality of points may be provided to simulate a surface, including contours, superimposed on the patient 14. The user 12 may view the mixed reality image through the MR device 16, but may not view the complete rendered 3D MR image 18*a* on the patient 14 during the verification in block 250. The user 12 may view the verification image in block 250 that is superimposed onto the patient 14 to the MR device 16 to verify registration.

The user 12 may then confirm registration in block 260 through various inputs. In confirming the registration by the user 12, in block 260 the user 12 may move the instrument 94 (or the instrument may be a probe or non-invasive instrument) to various portions of the patient 14 in real space. In moving the instrument 94 over the patient 14, the processor system 26 may receive tracked location information of the instrument 94 and create or generate the icon 22. The icon 22 may be displayed at the tracked location with the MR device 16 and the user 12 may view the patient 14 and the icon 22 and also the instrument 94. The user 12 may view or determine that the icon 22 is at the same location as the instrument 94 to receive a visual confirmation that registration is proper or correct. For example, the user 12 may view that the icon 22 is substantially superimposed over the instrument 94 and at a location that the user 12 is pointing the instrument 94 relative to the patient 14. If registration is not proper or correct (e.g., greater than about 0.5 millimeters (mm) to about 3 mm between the viewed instrument 94 and the icon 22) the user 12 may instruct the processor system to further refine registration.

After verifying registration in block 250 and user confirmation of registration in block 260, if selected, the registration process may end in block 270. As noted above, registration allows for the MR image 18*a* to be displayed relative to the patient 14 in a substantially precise manner. Therefore, the displayed anatomical and physiological features in the MR image 18*a* may be viewed by the user 12 at the same anatomical location (e.g. within about 0.1 mm to about 2 mm from the actual real world position) on the patient 14 as they exist in the MR image 18*a*.

As noted above, the MR image 18*a* may include various features. For example, the MR image 18*a* may include a photographic image of the subject 14 that is superimposed on the subject 14. Further, the MR image 18*a* may include a physiological or anatomical data, such as blood vessel locations, sulcus locations, hard tissue or other soft tissue locations and positions, or disease processes. For example, the MR image 18*a* may include an identification of a tumor to be resected, biopsied, etc. In various embodiments the MR image 18*a* may include identified location of a tumor in the brain of a patient 14 and one or more trajectories to reach the tumor for the resection. Therefore, in registering the MR image 18*a* to the subject 14, the position of the tumor identified in the MR image 18*a* may be identified for the user 12 on the patient 14 with the MR device 16.

As discussed above, the system illustrated in the operating room 10 in FIG. 1 may be used to perform procedures on the subject 14. It is understood, however, that the procedures performed on the subject 14 may be non-surgical or non-medical procedures including the subject 14 not being a human or other living subject. Nevertheless, in various embodiments, the procedure being performed on the subject 14 may be a navigated procedure including a procedure to remove a brain tumor or perform other resections or procedures in a brain of the subject 14. Regardless of the specific procedure, however, the user 12 may view the subject 14 in a mixed reality manner using the MR device 16. As noted above and illustrated in FIGS. 2, 2A, and 3, and further illustrated in FIGS. 5 and 6, the user 12 may view the MR image 18*a* in combination or in addition to the subject 14. In various embodiments, the MR device 16 or one substantially identical or similar thereto may be used by a user not in the operating room 10 to view at least the MR image 18*a*. For example, a chief surgeon may view the MR image 18*a* at a location remote from the operating room 10 that the user 12 is viewing in the operating room 10. The processor system 26 may transmit the MR image 18a to a remote location to be processed by a separate processing system and/or the same processing system 26 to display on a remote MR display to be viewed by a remote user. In this way, the remote user may assist the in-room user 12 for selecting an entry point, identifying a tumor, reviewing a surgical path or trajectory, or other appropriate assistance to the user 12.

The viewing of the MR image 18a relative to the subject 14 may be based on the registration of the image to the subject 14, as discussed above. Further, the illustration of the various icons, as discussed herein, may be due to tracking instruments with the tracking systems that may include one or more of the localizers 80, 82. It is further understood, however, that the range finding or other locating system incorporated into the MR device 16 may be used to track various portions, including the user's hands 12a, 12b and display icons or information relating to the tracked position. The range finding system 221 may determine the position of the tracked portions (with or without a tracking device trackable by the localizer of the tracking system) relative to the subject 14 and or the MR image 18a. Further, the range finding system or other appropriate position determining system of the MR device 16 may be the only tracking system and transmit the location information to the processing system 26 for display on the subject 14 and/or the MR image 18a with the MR device 16.

Figure 6:
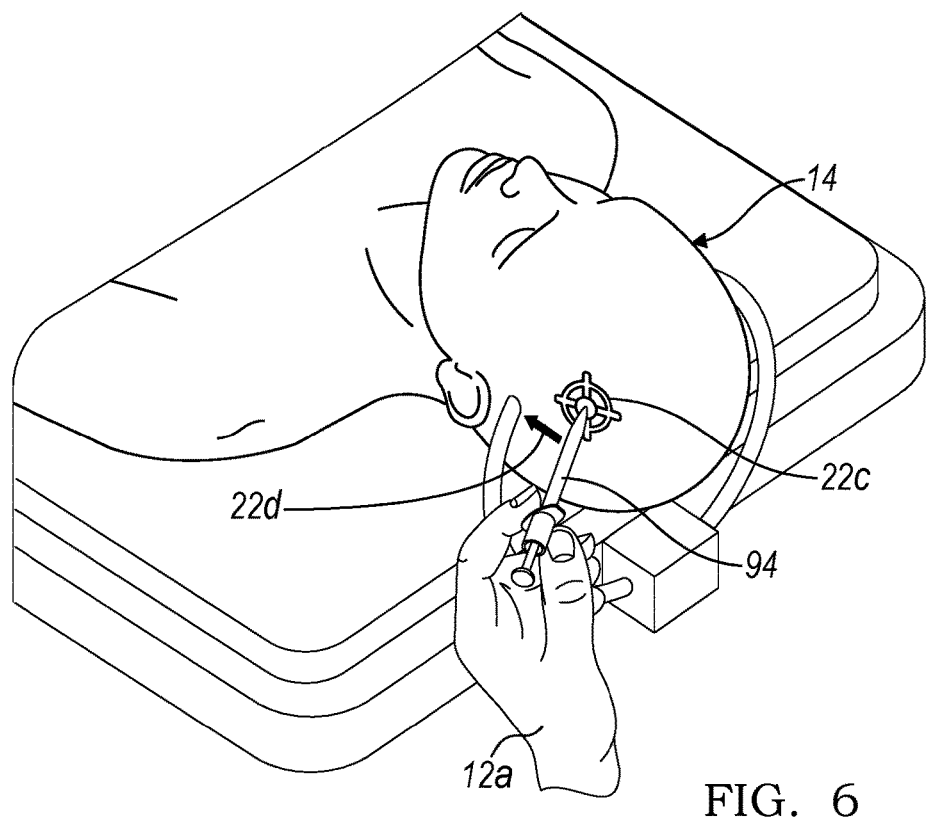
FIG. 6 is a user's perspective view using the MR device to view a real object and an image, according to various embodiments.
Figure 6A:
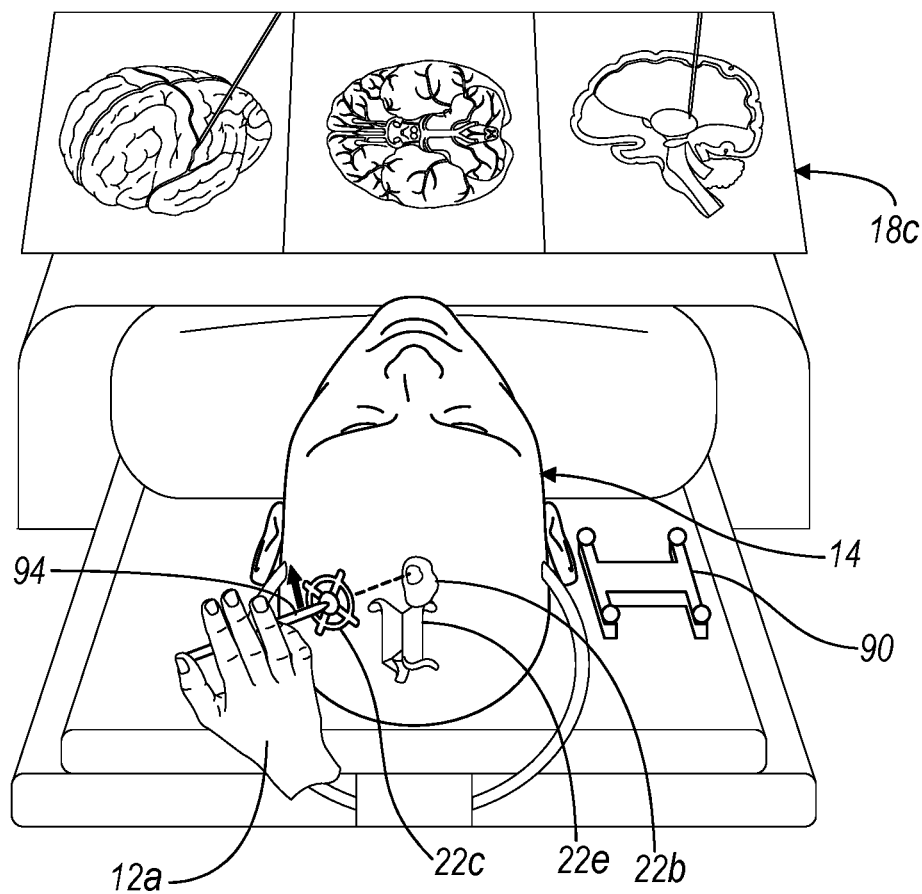
FIG. 6A is a user's perspective view using the MR device to view a real object and an image, according to various embodiments.

With reference to FIGS. 3, 6, and 6A, the user 12 viewing the subject 14 through the MR device 16 may also view various icons and images in addition to the MR image 18a that is registered to the subject 14. The registration process, as discussed above, may be used to register all image data relative to the subject 14. As noted above, the subject 14 may also be tracked with the DRF 90. Further, the subject 14 may be tracked or identified and located in space relative to the MR device 16 using the various area scanning technologies associated with the MR device 16, as discussed above.

Thus, the user 12 may view the subject 14 through the MR device 16 to view the icon 22. The icon 22 may be included as one or a plurality of icons displayed simultaneously or as selected by the user 12. For example, an instrument icon 22a may be illustrated superimposed on the patient 14. As discussed above, the instrument icon 22a may be superimposed on the MR image 18a or without the MR image 18a and appear substantially directly on the patient 14. Further, the user 12 may also view the real world through the MR device 16, including the instrument 94 that is viewable outside of the patient 14 and the user's hand 12a. It is understood that the user 12 may also view other portions of the real world in addition to the instrument 94 and the user's hand 12a.

The displayed icon 22, such as the instrument icon 22a may illustrate either a current tracked location of the instrument 94 or an extension or projected path of the instrument 94. For example, as illustrated in FIG. 3, the icon 22a may illustrate a portion of the instrument 94 that is within the skull or brain of the patient 14 or may illustrate a path on which the instrument 94 is currently aimed. As understood by one skilled in the art, the instrument 94 may include a biopsy needle that may be held in a stage that defines a trajectory that the needle will travel. Therefore, the instrument icon 22a may illustrate a path that the instrument 94 will take if moved along a straight line along a current axis of the instrument 94. The icon 22a may have different portions (e.g. differently colored portions) that illustrate the current or projected position of the instrument 94. The MR device 16 may illustrate various colors to identify different features being displayed by the MR device.

Other icons may include a tumor icon 22b. The tumor icon 22b may be any appropriate icon that may be used to illustrate portions of the anatomy of the patient 14. With brief reference to FIG. 6A, anatomy icons may also include other anatomy icons 22e which may illustrate blood vessels or sulci. Accordingly, it is understood that various portions of the image data may be segmented and displayed with the MR device 16 superimposed on the patient 14 once the image data is registered to the patient 14.

Returning reference to FIG. 3 and with additional reference to FIG. 6, the MR device 16 may also include an entry point icon 22c displayed superimposed on the patient 14 and also an instructional or directional icon 22d. As discussed above, the entry or target icon 22c may be a proposed or planned entry point for entering into the patient 14. As discussed above, a selected procedure may include removal or biopsy of a tumor illustrated by the tumor icon 22b in the patient 14. A remote user, such as the chief surgeon, may assist in moving or verifying the entry point icon 22c illustrated relative to the subject 14.

The directional or instructional icon 22d may be an icon presented by the processor system 26 automatically and/or by the remote user to assist the in-room user 12 in positioning the instrument 94 at a selected or predetermined (e.g., preplanned) location. As discussed above, various procedures may include preplanning that include various preplanned or predetermined features such as entry points relative to the subject 14, trajectories of instruments relative to the subject 14, and other appropriate features. These features may be saved in the memory system 30 or any appropriate memory system accessible by the processor 32. Therefore, the instrument 94, which is tracked as discussed above, may be tracked relative to the entry point that is illustrated by the entry icon 22c. The processor system 26, by tracking the instrument 94, can provide the directional icon 22d to the user 12 with the MR device 16 to indicate a direction to move the instrument 94 to place it on the preplanned path. It is understood that the directional icon 22d may not be a requirement, and may simply be provided to indicate a direction of movement to place the instrument 94 at the preplanned trajectory or other position relative to the patient 14. The directional icon may be superimposed on the MR image 18a and/or superimposed on the real world without the MR image 18a as illustrated in FIG. 6. Regardless, the MR device 16 allows the icons to be displayed to the user 12 while the user 12 is also able to view the subject 14. Therefore, the icons may provide a real time and intuitive display and analysis for the user 12.

In addition to icons 22 and other information, such as the MR image 18a, additional image data or other data may be provided in the MR display 16. With reference to FIG. 6A, two-dimensional or non-three-dimensional image data may be displayed in the field of view of the user 12, but away from the subject 14. As illustrated in FIG. 6A, two-dimensional images 18c may be displayed for viewing by the user 12 for various purposes. As noted above, preplanned procedures may include trajectories and entry points and the user 12 may view these as two-dimensional images while also viewing the patient 14 through the MR device 16, as illustrated in FIG. 6A. Therefore, the user 12 may view a plurality of type of data substantially simultaneously through the MR device 16 without attempting to view the patient 14 separate from the display 20, as illustrated in FIG. 1.

In addition to performing the actual procedure, as noted above, the image data acquired with the imaging system 25 may be processed with the processing system 26, or other appropriate processing system, for viewing with the MR display 16 without the subject 14 in place. For example, as illustrated in FIG. 6A, the two-dimensional image data 18*c* may be viewed separate from the patient 14. Further, the MR image 18*a* may be viewed without the subject 14 in place. Therefore, the image data may be acquired of the subject 14 and may be viewed with the MR device 16 for various planning, confirmation, and the like stages prior to performing any procedure or entering the operating room 10.

Also, during the planning for a procedure and/or during a procedure various different types of image data may be displayed. As noted above, only the icons representative of the tumor may be displayed, however, various selected portions of the image data may be segmented and displayed at the appropriate location relative to the subject 14 with the MR device 16 based upon the registration of the image data to the subject 14. For example, in planning or performing a procedure, blood vessel image data or functional image data (e.g. functional MRI data and PET data) may be displayed to allow a user to view blood vessels near or in a trajectory of the instrument 94 during a procedure, such as inserting an instrument 94 into the subject 14.

Further, the image data including the MR image 18*a* and the various icons 22 may be used during an operating procedure. As illustrated in FIG. 3, the instrument icon 22*a* may be used to illustrate the position of the instrument within the subject 14. The instrument icon 22*a* may be used to illustrate advancement of the instrument 94 to a selected area or target that is identified, such as within a tumor icon 22*b*. Therefore, the user may view the instrument icon 22*a* and the tumor icon 22*b* to determine placement of the instrument 94 within the tumor in the subject 14. Various procedures may occur, such as resection or ablation of the tumor, biopsy of the tumor, or the like. For example, the instrument icon 22*a* may be used to illustrate the position of the instrument relative to the tumor illustrated by the tumor icon 22*b* for obtaining a biopsy of a tumor within the subject 14. The icons may be viewed through the MR device 16 while the user 12 is also viewing the subject 14.

The MR device 16, noted above, may be used for various types of procedures. As noted above, the user 12 may wear the MR device 16 during a selected procedure, including during an operative phase and various preplanning or interoperative phases or portions.

In various embodiments, the MR device 16 may be used to view various types of markers or biomarkers that are only visible or fluorescent under specific wavelengths that are generally not viewable either by humans and/or under normal illumination. For example, fluorescence may be viewable due to a ALA-ppIX that has gathered in a selected region (e.g., a tumor) of the subject 14. Even during an open operation procedure, various tissues, such as tumorous tissues, may be difficult to distinguish from surrounding or healthy tissue. Various luminescent materials may be provided to the patient 14 either during or prior to a procedure and may gather within a portion of the subject 14, such as the tumor. These markers may not be luminescent or viewable under normal lighting conditions. Therefore, the lights may be turned off in an operating room to allow viewing of the luminescent markers. Once the illumination is returned to normal the marker may be nearly invisible.

The MR device 16 may display an image based upon the displayed luminescent marker at an initial period to allow for the user 12 to view a mixed reality image combining both an image of the tissue with a luminescent marker even under normal operating room lighting conditions. For example, as illustrated in FIG. 3, the tumor icon 22*b* may be an illustration of the tissue that has the marker viewed by the user 12 under special lighting conditions. Under normal lighting conditions, the icon 22*b* may be maintained in the field of view of the user 12 due to the MR device 16. Therefore, the user 12 can view the mixed reality image of the icon 22*b* and the tissue of the subject 14 simultaneously even under normal lighting conditions.

In various procedures, monitoring of nerve integrity may be selected or helpful. Neural or Nerve Integrity Monitoring (NIM®) monitoring systems can include the Medtronic NIM-Eclipse® Nerve Monitoring System sold by Medtronic, Inc., having a place of business in Minnesota, USA. During various procedures, the user 12 may stimulate neural matter, including brain tissue or spinal nerves and view or otherwise receive an indication of nerve reaction in the subject 14. For example, during a selected procedure, the user 12 may be viewing brain tissue of the subject 14. The user 12 may stimulate a portion in the brain and determine that a selected muscle group in the subject 14 is stimulated, such as a left leg. The user 12, upon viewing the stimulation reaction in the subject 14, may have the stimulated portion of the brain identified in the MR device 16 at the location on the patient 14. For example, with reference to FIG. 6, rather than identifying an entry point of the icon 22*c*, the icon 22*c* may indicate a portion of brain tissue that was stimulated when a selected response occurred. The icon color, shape, and the like, can be used to annotate the region of the brain as to the specific muscle having responded to the stimulation provided in the brain tissue. The indication by the icon can be maintained in the field of view of the user 12 due to wearing the MR device 16 and the MR device 16 having identified or located the tissue in the patient. Thus, the MR device 16 may be used to provide an indication to the user of the regions in the brain that relate to specific tissues or regions of the anatomy that are stimulated or controlled by various nerve bundles or cortical regions.

In various other embodiments, the navigation system including an MR device 16 may be used to assist in substantially emergency or emergency situations. For example, cerebral spinal fluid (CSF) drainage may be necessary and a shunt placement may be prescribed. A shunt placement may also be assisted by viewing or identifying various tissues in the subject 14 for performing the procedure.

As discussed above, the imaging system 25 may include the O-Arm® Imaging System sold by Medtronic, Inc. The O-Arm® imaging system may acquire image data that is automatically registered or localized relative to the subject 14, as described in U.S. Pat. No. 9,412,200, incorporated herein by reference. Briefly, the O-Arm® imaging system may be operated to acquire image data at substantially precise known positions relative to the subject 14. This image data may be used to generate images, such as the MR image 18*a*, for viewing relative to the subject 14. Due to the auto-registered or auto-localized image data, the displayed MR image 18*a* on the MR device 16 may also be automatically registered relative to the subject 14. As discussed above, the MR device 16 may include a range finding system such as a 3D surface scanning or other range finding system (e.g. radar, lidar, ultrasound, laser, stereoscopic cameras) to determine its position relative to other features in real space. As the MR device 16 is worn by the user 14, the MR device 16 may be used to determine its position relative to the imaging device 25 or other features and objects in a selected volume. Therefore, as the image data acquired with image device 25 is automatically localized or registered to the subject 14 and the MR device 16 knows its position relative to the subject, the MR image 18a displayed with the MR device 16 for viewing by the user 12 is also registered to the subject 14.

The MR device 16, including the range finding system, may also be able to determine with the processing system the location of the MR device 16 to selected or specific markers that are placed in a selected volume. The specific markers may be recognized by the range finding system and used to identify and recall locations of objects in the space. For example, specific markers (e.g. reflective cubes) may be placed on walls, ceilings, etc. to recall and orient the MR device 16 to the volume in which it is presently located, even if removed for a period of time.

The processing systems 26 may also include other instructions that may be used to automatically identify or segment various portions of the anatomy. For example, for a CSF drainage and/or shunt placement, the processor system 26 may substantially automatically segment and illustrate ventricular anatomy based upon CSF in and near the brain tissue and surrounding brain tissue. In this manner, the MR device 16 may illustrate or display the MR image 18a as a three-dimensional model, as discussed above, in substantially 1:1 scale with the subject 14 to illustrate both the brain tissue matter and the segmented regions. The user 12 may then plan, with the MR image 18a, a procedure for positioning a shunt in the subject 14 to assist with CSF drainage.

For example, the user 12 may position the instrument 94 that may be tracked with the tracking system, including the localizer 80, 82. As the image data is automatically registered with the imaging system 25, the position of the instrument 94 may be displayed on the MR image 18a displayed with the MR device 16 worn by the user 12. The user 12 may view the instrument icon 22a as a projected position for the instrument within the subject 14 as superimposed on the MR image 18a. Therefore, the user 12 may quickly and effectively understand a result of a proposed position and/or trajectory for performing a shunt placement. Moreover, during the planning, the user 12 may move the instrument 94 to attempt to visualize alternative or different positions and/or trajectories to achieve placement of a shunt.

The user 12 may then identify or command the processing system 26 to save a selected or identified trajectory and display it on the MR image 18a, similar to that discussed above. For example, once identified, the instrument icon 22a may be changed to a trajectory icon 22t and displayed on the MR image 18a for viewing by the user 12 during a procedure of placing a shunt. The user 12 may then use the selected trajectory icon 22t to also determine placement and formation of the burr hole and/or placement of a guide for placing a shunt in the subject 14. Once the burr hole has been formed, then a tracked instrument may be used to position the shunt in the subject 14 and the tracked location of the instrument may be identified with the instrument icon 22a on the patient 14 with or without the MR image 18a. Once the shunt has reached the selected position of the shunt, it may be identified automatically due to tracking of the instrument 94 and a message may be provided to the user 12 based upon tracking the instrument 94. The user 12 may identify a planned location for the shunt and the processor system 26 may automatically identify when the shunt reaches the planned position. In addition, or alternatively thereto, the user 12 may view the tracked location by viewing the instrument icon 22a on the subject 14 with or without the MR image 18a and the user 12 may identify when the shunt is properly positioned.

Regardless, the image data acquired with the imaging system 25 may be substantially automatically localized due to the imaging system 25 and being able to plan and view a procedure with the MR device 16 may allow for the efficient and rapid placement of a shunt or other selected emergent procedures.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system to view an image relative to a subject, comprising:

a display device having (i) a display portion and (ii) a transparent portion, wherein the transparent portion is configured so that a user viewing the subject through the display device is able to view both (i) the subject and (ii) the image relative to the subject;

a tracking system having a localizer and a tracking device; and a processing system configured to execute instructions to determine a tracked location of the tracking device and generate an icon for display with the display device to represent the tracked location of the tracking device relative to the subject;

a wearable device, separate from the tracking system and configured to be worn by the user, including (i) the display device and (ii) a range finding device also separate from the tracking system;

an imaging device separate from the wearable device operable to acquire the image for display with the display device;

wherein the range finding device is configured to scan the surface of the subject and obtain a point cloud of the subject to define three-dimensional coordinates of the subject;

wherein the processing system is configured to determine a size and scale of the subject using the three-dimensional coordinates of the subject from the range finding device at least via the scan and register the image to the subject by the processing system using the three-dimensional coordinates of the subject from the range finding device at least via the scan to identify at least one point in a subject space to correlate to pixels or voxels in the image to register the image to the subject;

wherein the processing system is configured to register the image to the subject by the processing system using the three-dimensional coordinates of the subject from the range finding device at least via the scan to identify at least one point in a subject space to correlate to determined pixels or voxels in the image to register the image to the subject;

wherein the localizer is configured to track the tracking device in three-dimensional space relative to the subject to allow the generated icon related to the tracked location of the tracking device to be displayed with the display device; and wherein the display device, based on the registration of the image to the subject, is operable to display the image and the icon such that the view of the user is a mixed reality view such that the image is configured to be perceived as appearing in the same space as the subject.

2. The system of claim 1, wherein the scan of the surface of the subject that is configured to identify at least one point in the subject space is a real space defined relative to the subject and the image defines an image space by the pixels or voxels in the image;

wherein the image is configured to be registered to the subject at least by the processing system executing instructions to perform a transformation between the three-dimensional coordinates of the subject and three-dimensional coordinates of the image;

wherein the three-dimensional coordinates of the subject are determined relative to the wearable device with use of the range finding device;

wherein the system is operable to receive an input from the user so that the image is registered to the subject and provide feedback to the user as at least one of audio or visual cues to assist in and for confirmation regarding registration of the image to the subject.

3. The system of claim 2, further comprising:

an instrument associated with the tracking device;

wherein the tracking system is configured to track the instrument via the tracking device;

wherein the icon representing a tracked location of the instrument relative to the patient is operable to be displayed with the display device;

wherein the display portion of the display device includes an alterable display that is configured to be driven by the processing system.

4. The system of claim 3, further comprising:

a non-wearable display;

wherein the wearable device is head mounted on the user and the non-wearable display is spaced a distance from the user.

5. The system of claim 4, wherein the wearable device is configured to display the image relative to the subject as a three-dimensional image.

6. The system of claim 5, wherein the three-dimensional image is the mixed reality image that is configured to be perceived as appearing in the same space as the subject.

7. The system of claim 2, wherein the processing system is further configured to:

determine with the range finding device a position of the wearable device relative to the imaging device; and generate the image based on the acquired image data with the display portion of the wearable device based on the determined position of the wearable device relative to the imaging device and the acquired image data that is automatically registered to the subject.

8. A system to display an image to a user relative to a subject, comprising:

a wearable mixed reality display device configured to be worn by the user having (i) a display portion and (ii) a range finding portion, wherein the display portion has a transparent portion configured so that the user wearing the wearable mixed reality display device is able to view both the subject and the image displayed with the display portion relative to the subject, wherein the range finding portion is configured to determine a plurality of subject space three-dimensional coordinates relative to the wearable mixed reality display device;

an imaging system to generate the image, wherein the imaging system includes an annular gantry and a known precise position of the imaging system relative to the subject is operable to be determined while acquiring the image;

a processing system configured to execute instructions to: (i) automatically register the image to the subject based at least on the known precise position of the imaging system relative to the subject while acquiring the image, (ii) determine a size and scale of the subject based on the plurality of subject space three-dimensional coordinates from the range finding portion, (iii) selectively assist registration of the image to the subject based on image three-dimensional coordinates and the plurality of subject space three-dimensional coordinates from the range finding portion, (iv) determine a tracked location of a trackable portion separate from the wearable mixed reality display device, and (v) generate an icon to be displayed with the wearable mixed reality display device to represent the tracked location of the trackable portion relative to the subject; and a registration input member and a feedback system configured to provide an instruction and output at least one of visual or audio cues to the user to at least one of assist or confirm the registration of the image to the subject, wherein the registration allows the image to be perceived by the user of the wearable mixed reality display device as appearing in the same space as the subject;

a user input configured to receive input from the user regarding at least the registration of the image to the subject and receive a hand input;

wherein the range finding portion is configured to scan the surface of the subject and the processing system is configured to register the image to the subject at least based on a correlation of determined portions of the image to register the image;

wherein the display portion, based on the registration of the image to the subject, is operable to display the image such that the user views a mixed reality including the image perceived by the user as appearing in the same space as the subject and the icon that is the tracked location of the trackable portion.

9. The system of claim 8, wherein the display portion of the wearable mixed reality display device is operable to be configured to display the image separate from the subject prior to or after a registration of the image to the subject;

wherein registration input member includes a tracked instrument moveable by the user relative to the subject to confirm the registration;

wherein the registration input member is operable to receive an input from the user to at least one of perform or assist in the registration.

10. The system of claim 9, wherein the range finding portion is configured to determine three-dimensional coordinates relative to the wearable mixed reality display device of the trackable portion to track the trackable portion for determining the tracked location of the trackable portion;
wherein the display portion is configured to display an instrument icon relative to the image based on the range finding portion tracking the trackable portion.

11. The system of claim 10, further comprising:
a tracking system, separate from the wearable mixed reality display device having the range finding portion, having a localizer and a tracking device, wherein the localizer is configured to track the tracking device at a tracking device position relative to a subject position of the subject;
an instrument having the tracking device;
a confirmation system, wherein the confirmation system is configured to provide a display of a confirmation of a position of the tracked instrument;
wherein the instrument includes at least one of a shunt, a biopsy needle, an ablation catheter, a resection instrument, a stimulation probe, navigation probe, or combinations thereof;
wherein the display of the icon is determined based on the tracking of the tracking device.

12. The system of claim 11, further comprising:
a planning input to input a surgical plan based on viewing the image with the display portion;
wherein the icon is operable for preparing the surgical plan;
wherein a memory system is configured to store the surgical plan including at least a trajectory of an instrument that is the trackable portion;
wherein the processing system is configured to recall the surgical plan.

13. The system of claim 11, further comprising:
an additional tracking device operable to be positioned relative to the subject;
wherein the processing system is configured to execute further instructions to identify the additional tracking device.

14. The system of claim 8, wherein the user input includes an audio input;
wherein the processing system is configured to operate at least the display portion and the range finding portion of the wearable mixed reality display device;
wherein the audio input is configured to receive verbal commands from the user to instruct for at least displaying the image with the display portion and registering the image to the subject.

15. The system of claim 8, further comprising:
a remote wearable mixed reality display device having a display portion, wherein the display portion is configured for a remote user wearing the remote wearable mixed reality display device to view the image as viewed by the user with the wearable mixed reality display device.

16. A method of operating a device for viewing an image relative to a subject, comprising:
configuring a wearable mixed reality display device having a display portion and a range finding portion such that the display portion has a transparent portion configured so that a user wearing the wearable mixed reality display device is able to view the subject and the image relative to the subject;
configuring the range finding portion to scan a surface of the subject to determine a plurality of subject space three-dimensional points relative to the wearable mixed reality display device;
acquiring the image of the subject from an imaging system and a position of the imaging system while acquiring the image relative to the subject;
executing instructions with a processing system based on received input from the user, after the scan of the surface of the subject to determine the plurality of subject space three-dimensional points, to determine a size and scale of the subject based on the determined plurality of subject space three-dimensional points, and to register the image to the subject by correlating pixels or voxels of the image and the determined plurality of subject space three-dimensional points;
receiving a registration input from the user by tracking an instrument as the registration input from the user to confirm the registration;
providing feedback as at least one of an audio or visual cues to the user regarding the input from the user regarding registration; and
operating the wearable mixed reality display device to display (i) the image and (ii) an icon representing a tracked location of a trackable device relative to the subject with the mixed reality display device such that viewing the image relative to the subject via the display portion allows the user to perceive the image as appearing in the same space as the subject based on the registration of the image to the subject space three-dimensional coordinates due to the scan of the subject.

17. The method of claim 16, further comprising:
instructing the user by the processing system to view the subject while wearing the wearable mixed reality display device including displaying an icon with the display portion viewable by the user.

18. The method of claim 16, further comprising:
tracking the trackable device with a tracking system separate from the range finding portion;
executing instructions with the processing system to determine the tracked location of the trackable device; and
displaying the icon with the wearable mixed reality display device to represent the determined tracked location, based on the tracking, of the trackable device relative to the subject and the registered image;
wherein executing instructions with the processing system to selectively register the image to the subject includes receiving the position of the imaging system while acquiring the image.

19. The method of claim 18, further comprising:
planning a surgical procedure by viewing the image with the wearable mixed reality display device including at least an entry point, target point, or a path from the entry point to the target point; and
saving the surgical plan with a memory system.

20. The method of claim 19, further comprising:
operating the processing system to recall the surgical plan; and
displaying an icon with the display portion of the worn wearable mixed reality display device representing at least one of the achievement of the saved surgical plan or a warning regarding selected structures of the subject.

21. The method of claim 20, further comprising:
obtaining automatically registered images of the subject at least by having operated the imaging system to acquire image data at substantially precise known positions relative to the subject;
displaying the obtained automatically registered images of the subject with the wearable mixed reality display device;
tracking a location of a stent; and
viewing the icon with the wearable mixed reality display device to represent the tracked location of the stent superimposed on the displayed automatically registered images of the subject.

22. The method of claim 16, further comprising:
tracking a separate tracking device with a tracking system that is separate from the range finding portion;
executing instructions with the processing system to determine a tracked location of the separate tracking device; and
displaying the icon with the wearable mixed reality display device to represent the determined tracked location, based on the tracking, of the separate tracking device superimposed on the registered image.

23. The method of claim 22, further comprising:
tracking a location of a stimulating instrument;
stimulating a portion of the subject with the stimulating instrument to cause a response of the subject; and
displaying an icon with the wearable mixed reality display device as superimposed on the subject to annotate the stimulated portion of the subject;
wherein the icon indicates a portion of tissue that was stimulated when the response occurred.

24. The method of claim 22, further comprising:
saving a view of a fluorescing portion of the subject while wearing the wearable mixed reality display device;
displaying a representation of the saved view of the fluorescing portion of the subject after saving the view of the fluorescing portion with the wearable mixed reality display device superimposed on the subject.

25. The method of claim 16, further comprising:
instructing the range finding portion to scan a hand of the user to determine a position of the hand relative to the image displayed with the display device;
wherein instructing the processing system to execute instructions to selectively register the image to the subject includes the user moving, by at least the tracking of the hand, the image to a selected starting point for the registration.

26. The method of claim 16, further comprising:
instructing the range finding portion to scan an instrument relative to the subject and the range finding portion to track a location of the instrument; and
displaying an icon representing the instrument with the display device relative to the image based on the scan of the instrument.

27. The method of claim 16, further comprising:
determining with the range finding portion a position of the wearable mixed reality display device relative to an imaging device; and
displaying the image based on the acquired image data with the display portion of the wearable mixed reality display device based on the determined position of the wearable mixed reality display device relative to the imaging device and the acquired image data that is automatically registered to the subject.

* * * * *

UNITED STATES PATENT AND TRADEMARK OFFICE
CERTIFICATE OF CORRECTION

PATENT NO. : 11,839,433 B2
APPLICATION NO. : 15/272808
DATED : December 12, 2023
INVENTOR(S) : Timothy J. Schaewe et al.

It is certified that error appears in the above-identified patent and that said Letters Patent is hereby corrected as shown below:

In the Specification

Column 1, Background, Line 21, Delete "57®" and insert --S7®-- therefor

Column 10, Detailed Description, Line 22, After "range", delete "are"

Column 16, Detailed Description, Line 65, Delete "14," and insert --12,-- therefor Signed and Sealed this
Twelfth Day of November, 2024

Katherine Kelly Vidal
*Director of the United States Patent and Trademark Office*